United States Patent
McGowan et al.

[11] Patent Number: 6,086,228
[45] Date of Patent: Jul. 11, 2000

[54] STERILE ILLUMINATED MAGNIFIER AND METHOD FOR SURGICAL USE

[76] Inventors: Michael J. McGowan, 3340 Davis Rd., Barrington, N.J. 08007; Shawn P. Mullen, 17 Foxridge Rd., Glenmore, Pa. 19343

[21] Appl. No.: 08/732,154

[22] Filed: Oct. 16, 1996

[51] Int. Cl.$^7$ .................................................. F21V 33/00
[52] U.S. Cl. .................... 362/396; 362/804; 362/253; 362/433; 607/88; 600/249; 359/802
[58] Field of Search .................................. 362/396, 804, 362/317, 430, 253, 285, 418, 433; 600/248, 249; 607/88, 90; 359/802; 606/120

[56] References Cited

U.S. PATENT DOCUMENTS

| | | |
|---|---|---|
| 758,741 | 5/1904 | Dunn . |
| 1,877,439 | 9/1932 | Wichart . |
| 2,093,457 | 9/1937 | Kuklin . |
| 2,104,198 | 1/1938 | Jones ........................................ 359/802 |
| 2,199,107 | 4/1940 | Kibbe ....................................... 359/802 |
| 2,394,231 | 2/1946 | Burski ...................................... 359/802 |
| 2,563,473 | 8/1951 | Levinson ................................. 359/802 |
| 2,641,965 | 6/1953 | Valenza ................................... 359/802 |
| 3,609,335 | 9/1971 | Kelly ....................................... 362/804 |
| 4,298,921 | 11/1981 | Krogsrud et al. . |
| 4,506,317 | 3/1985 | Duddy . |
| 4,540,239 | 9/1985 | Frankel ................................... 359/802 |
| 4,630,185 | 12/1986 | Copeland . |
| 4,885,667 | 12/1989 | Selden .................................... 362/396 |
| 5,041,954 | 8/1991 | Forrest, Jr. . |
| 5,163,752 | 11/1992 | Copeland et al. . |
| 5,664,875 | 9/1997 | Hegedus ................................. 362/191 |

Primary Examiner—Thomas M. Sember
Attorney, Agent, or Firm—Orrick Herrington & Sutcliffe LLP

[57] ABSTRACT

In accord with one aspect of the invention, an apparatus for illuminating and magnifying an object in a sterile field for observation is provided. A holder is mounted at one end of a base assembly. A magnifying lens is mounted to the holder and defines a field of vision. A light is attached to the holder by an attaching means in a predetermined spatial relationship with the lens such that the light directs a beam of light into the field. A method is provided for illuminating and magnifying an object in a sterile field without contaminating the sterile field. The base assembly and the holder are sterilized. The base assembly is positioned in the sterile field. A sterile pack containing the light in a sterilized condition is opened and the light is moved into the sterile field. The light is inserted into the opening of the holder. The light is actuated and provides a light beam. The magnifying lens is removed from a sterile pack and moved into the sterile field. The lens is attached to the holder in a predetermined spatial relationship with the light such that the lens defines a field of vision which the light beam intersects. An object is brought into the field of vision.

16 Claims, 5 Drawing Sheets

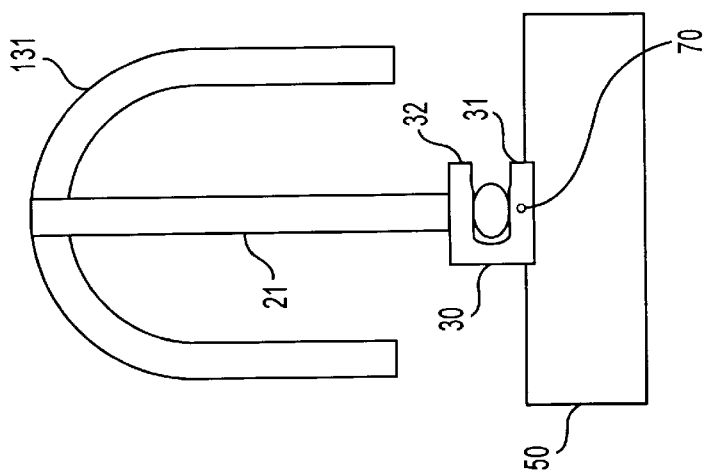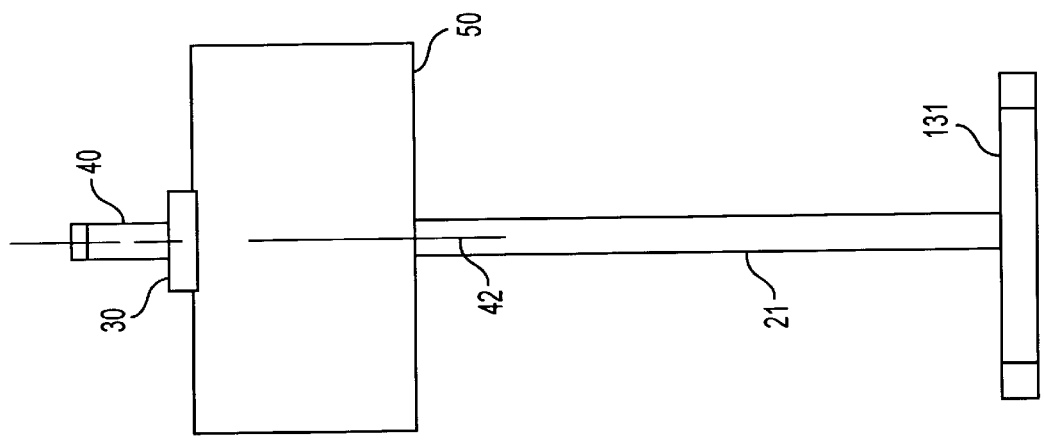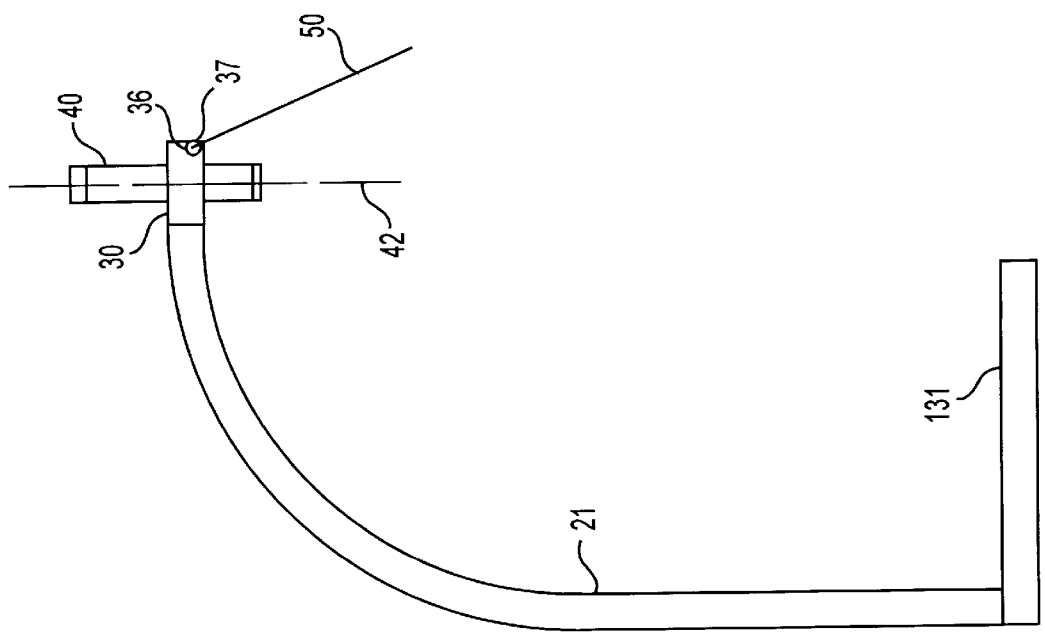

STERILE ILLUMINATED MAGNIFIER AND METHOD FOR SURGICAL USE

BACKGROUND OF THE INVENTION

This invention is related to the field of surgical equipment. In particular, the invention is directed to a sterile apparatus for illuminating and magnifying objects in a sterile field, and methods of using the apparatus.

In a surgical setting, such as an operating room, many scopes are employed to allow the surgeon to see into the patient's body and elsewhere. To improve the surgeon's view, the lights are dimmed in the rest of the surgical area. This reduces the glare and light distractions to the surgeon. Unfortunately, this also reduces the light for others in the surgical area to see. Certain members of the surgical team who are not in the sterile field can use simple lights to see gauges and equipment. These lights typically are not sterile and thus cannot be introduced into the sterile field. Members of the surgical team in the sterile field, such as the scrub nurse, must rely on nurses to hold a light for them or turn on an overhead light.

The difficulty seeing in a dark operating room is compounded by the small size of the objects to be viewed. In particular, surgical procedures requiring the use of scopes (e.g. laproscopy for gall bladder, colon, rectal, and gynecological conditions, neurological conditions, cataract, vitrectomy, etc.) often involve small incisions. These smaller incisions require smaller, more delicate "micro" instruments be used. In a darkened room, it can be particularly difficult to see these very small instruments.

Various lights have been developed over the years that allow a light source to be mounted to a fixed surface and manipulated by a user. For example, U.S. Pat. No. 4,506,317 discloses a magnetic support for a flashlight for use by an automobile mechanic. A magnetic base is attachable to an iron-containing surface. An elongated arm extends from the base and is attached to a C-shaped clamp which holds the flashlight. The arm can be pivoted and swiveled to direct the beam of light.

U.S. Pat. No. 5,163,752 is directed to a flashlight holder apparatus including a C-clamp to attach to a surface. An elongate, flexible tube extends from the C-clamp to a mounting plate on which the flashlight is secured.

U.S. Pat. No. 785,741 discloses a dental lamp. A light source is contained in a hood. A circular lens, which may be plano-convex or double convex, is located at one end of the hood. The light beam passes through the lens and is directed to a patient's mouth.

SUMMARY OF INVENTION

It is an object of the present invention to provide an apparatus and a method for illuminating and magnifying a field of vision in a surgical field.

It is an object of an aspect of the invention to provide an apparatus and method for illuminating and magnifying objects in a sterile field without requiring a nurse to actuate the light during use.

It is an object of an aspect of the invention to provide an apparatus and method for illuminating and magnifying objects in a sterile field, such as a surgical field, by directing a light beam into a field of vision under a magnifier, reducing extraneous glare to the surgeon.

It is an object of an aspect of the invention to provide an apparatus and method for illuminating and magnifying objects in a sterile field which can be quickly and easily sterilized, set up and positioned in the sterile field.

It is an object of an aspect of the invention to provide an apparatus and method for illuminating and magnifying objects in a sterile field which can be quickly and easily adjusted to better view objects in the sterile field.

In accord with one aspect of the invention, an apparatus for illuminating and magnifying an object in a sterile field for observation is provided. A holder is mounted at one end of a base assembly. A magnifying lens is mounted to the holder and defines a field of vision. A light is attached to the holder in a predetermined spatial relationship with the lens such that the light directs a beam of light into the field of vision.

Certain implementations of this aspect of the invention provide that: a pin is rotatably seated in a channel disposed in the holder, a cavity is disposed in the pin and the magnifying lens is seated in the cavity; the holder comprises a U-shaped member having a front arm and a rear arm, the rear arm is attached to the base assembly and the light is positioned between the front arm and the rear arm; the light and the magnifying lens is in a plane which intersects the axis of the light beam at an angle between 0° and 90°; the lens is in a plane which intersects the axis of the light beam at an angle of about 45°; the opening is shaped to actuate the light when the light; the base is a clamp, the clamp comprising a lower member fixed to the arm and a locking member selectively positioned on the arm by a ratchet; the arm further includes a swivel joint; the arm further includes a bending joint; the arm is flexible.

In accord with another aspect of the invention, a method is provided for illuminating and magnifying an object in a sterile field without contaminating the sterile field using an apparatus having a base assembly, a holder mounted at one end of the base assembly, a magnifying lens mounted to the holder, and a light mounted to the holder in a predetermined spatial relationship with the magnifying lens. The base assembly is positioned in the sterile field. A sterile pack containing the light in a sterilized condition is opened and the light is moved into the sterile field. The light is inserted into the opening of the holder. The light is actuated and provides a light beam. Similarly, the magnifying lens is removed from a sterile pack and moved into the sterile field. The lens is attached to the holder in a predetermined spatial relationship with the light such that the lens defines a field of vision which the light beam intersects. An object is brought into the field of vision.

Certain implementations of this aspect of the invention provide that: the base assembly and the holder are sterilized; the base assembly is sterilized in an autoclave; positioning the base assembly includes clamping the base assembly to a fixed surface; the light is actuated as it is inserted into the opening of the holder; attaching the magnifying lens to the holder comprises inserting an edge of the magnifying lens into a chamber on the holder; the light is contained in a light pack and the magnifying lens is contained in a lens pack.

Another aspect of the invention provides an apparatus for illuminating and magnifying a field of vision in a sterile field. An autoclavable holder is mounted at one end of an autoclavable base assembly and has a slot extending through the holder. A sterile light is selectively positioned in the slot in a first position or a second position wherein, in the first position, the light is off and, in the second position, the light directs a beam of light into a field of vision. A sterile magnifying lens is attached to the holder in a predetermined spatial relationship with the light.

Certain implementations of this aspect of the invention provide that the base assembly comprises a positionable arm and that a pin is fixedly mounted to an edge of the magnifying lens and is rotatably seated in a channel in the holder.

BRIEF DESCRIPTION OF THE DRAWINGS

FIGS. 4A–C are side, front and top elevation views, respectively, of an other embodiment of the apparatus for illuminating and magnifying an object in a sterile field;

DESCRIPTION OF PREFERRED EMBODIMENTS

Figure 1:
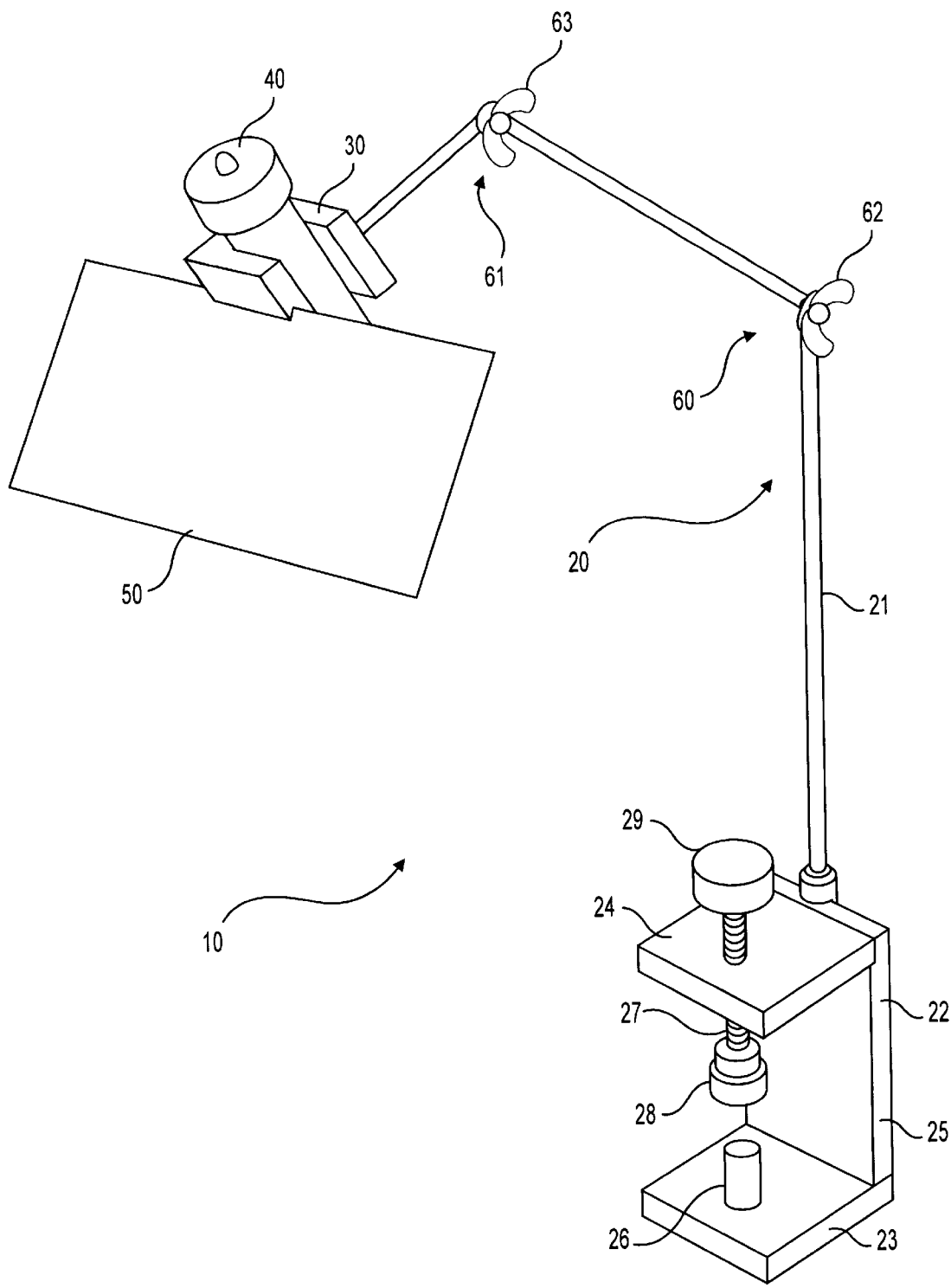
FIG. 1 is a front perspective view of an apparatus for illuminating and magnifying an object in a sterile field in accord with one aspect of the invention.

Referring to FIG. 1, an apparatus 10 for illuminating and magnifying an object in a sterile field in accord with an aspect of the invention is shown. A base assembly 20 includes a base 22 and an adjustable arm 21. A holder 30 is attached to the arm distal to the base. A light 40 is mounted to the holder. A magnifying lens 50 is also mounted to the holder and defines a field of vision. The light directs a beam of light into the field of vision.

The base assembly 20 and holder 30 are preferably autoclavable. The base assembly is preferably made of metal, such as stainless steel, and the holder is preferably made of plastic, such as Delrin. Of course, other materials, such as aluminum or other light weight materials, can be employed and still practice the invention.

As shown in FIG. 1, the base 22 is a clamp having a bottom plate 23 and a top plate 24 connected by a side plate 25. A post 26 extends up from the bottom plate. A bolt 27 is threaded into a hole in the top plate. A pad 28 is attached to the bolt on the end proximate the post. A knurled knob 29 is attached to the other end of the bolt. A support surface 100 (see FIGS. 3A and 3B) is positioned between the pad and the post. The knurled knob is rotated, causing the bolt (and the pad) to advance toward the post until the support surface is firmly held between the pad and the post.

Figure 3C:
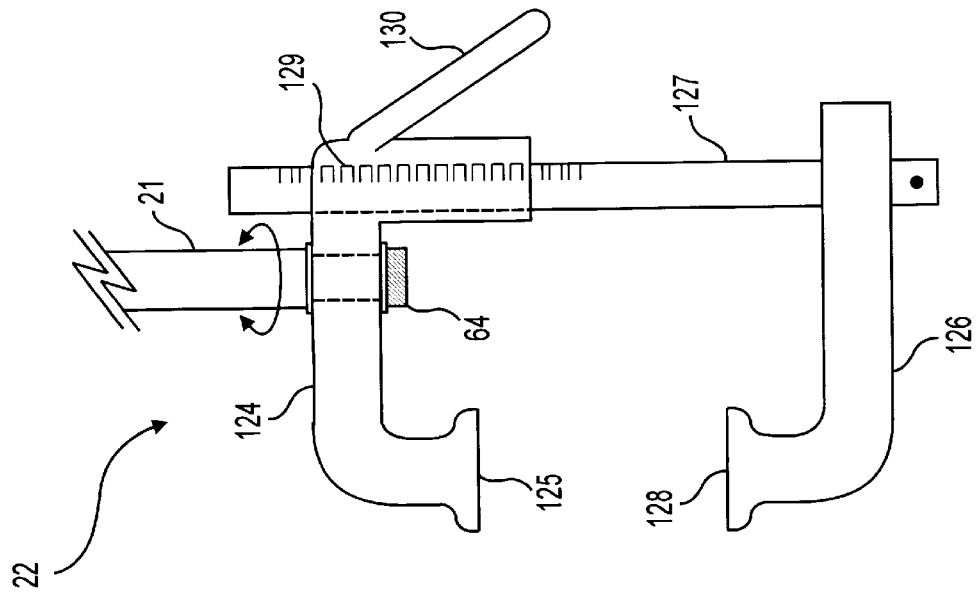
FIGS. 3A–C are side elevation views of base assemblies for use with the apparatus of FIG. 1.

Other types of bases may also be employed and practice the invention. Referring to FIG. 3C, the arm is mounted to a top bar 124. A top grip 125 is located at the end of the top bar. A lower bar 126 is connected to a rod 127. A lower grip 128 is located at the end of the lower bar and aligned with the top grip. The rod is connected to the top bar by a ratchet mechanism 129. Consequently, the rod can be slid toward the top bar, bringing the top grip and the bottom grip close about a support surface. After use, a lever 130 is turned, releasing the ratchet mechanism and allowing the rod to slide away from the top bar.

The base need not be a clamp to practice the invention. Referring to FIGS. 4A–4C, the base can be a simple stand, such as a U-shaped member 131. The arm is attached at the apex of the U-shaped member.

The arm is preferably adjustable and sized for convenient use. Currently, the arm is about 11 inches or 16 inches long. As shown in FIG. 1, the arm may include two pivot joints 60,61 that allow sections of the arm to be angled with respect to each other. Once in a desired position, wing nuts 62,63 can be tightened, locking the arm sections into a fixed position. Of course, other types of joints could be employed and practice the invention.

Figure 3B:
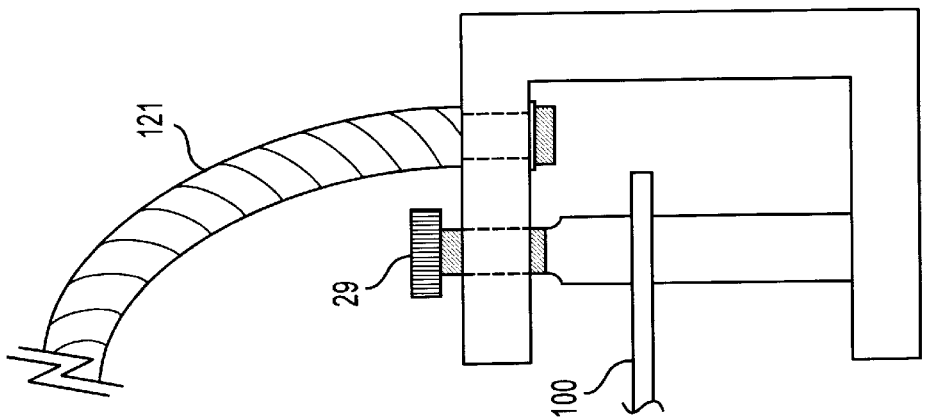
Figure 3A:
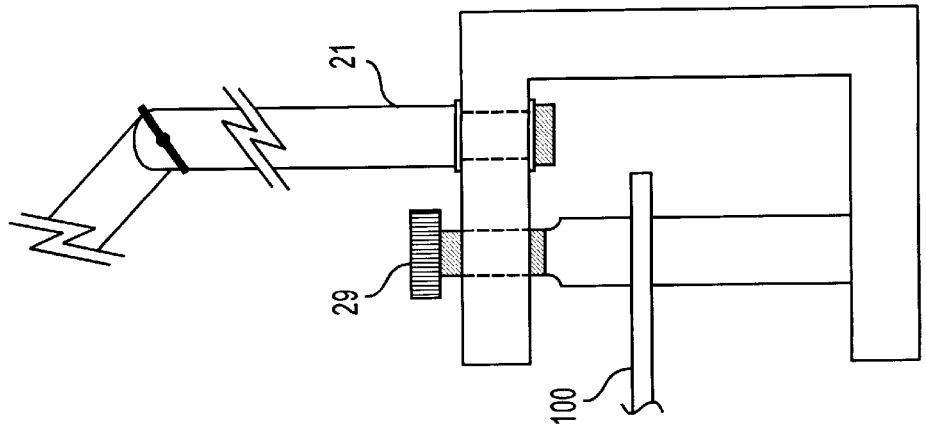

As shown in FIG. 3C, the arm 21 can be attached to the base 22 by a swivel joint 64 which permits the arm to rotate with respect to the base. Other swivel joints, or other rotating connections, can be inserted in the arm, allowing sections of the arm to rotate with respect to each other. For example, a swivel joint can be positioned on the holder 30 where it meets the arm, allowing the holder to be rotated. Further, various combinations of swivel and pivot joints may be employed as a particular application requires. The arm can also be made of a flexible bar 121 that can bend along its entire length, as seen in FIG. 3B.

Figure 2:
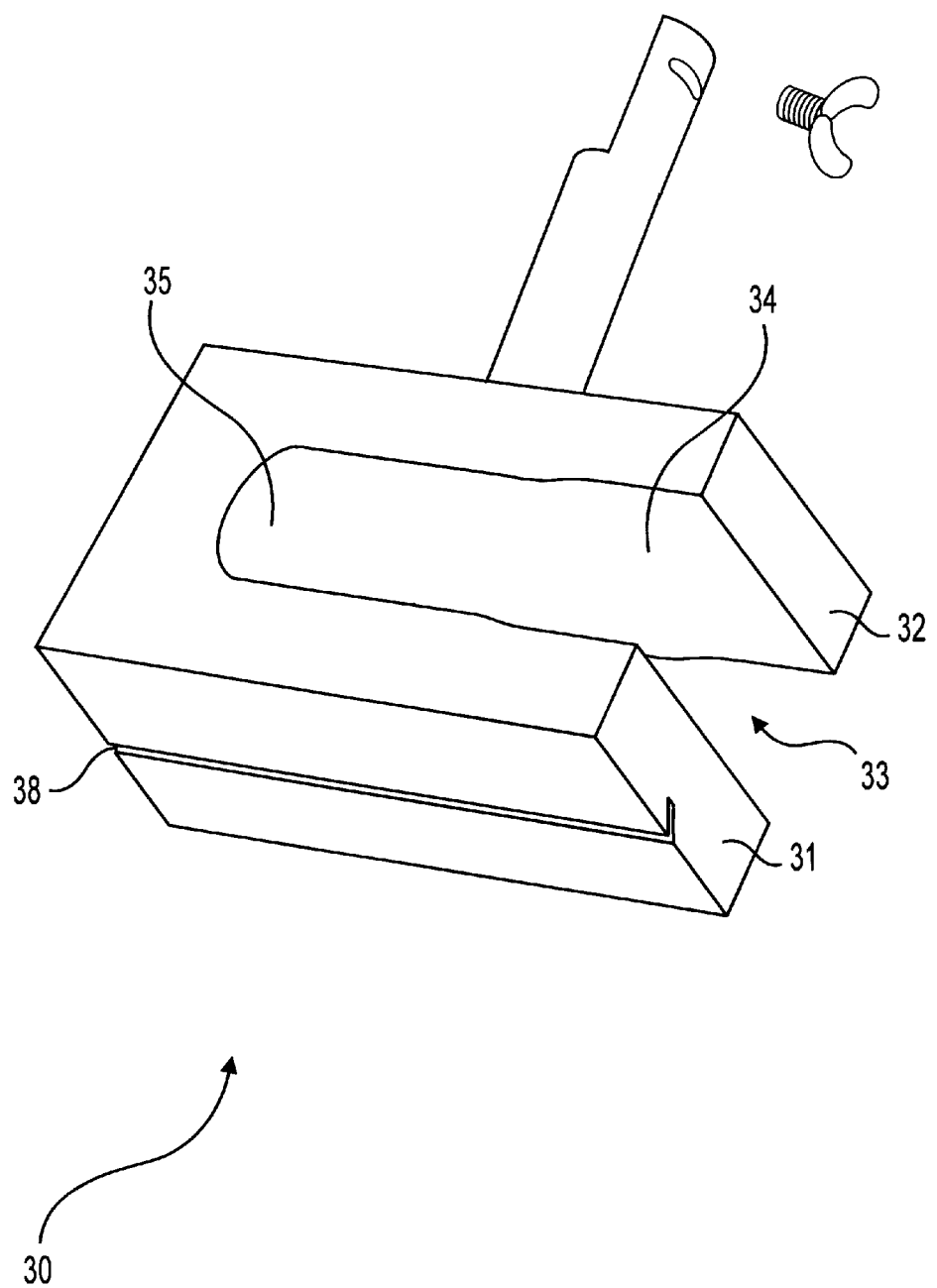
FIG. 2 is a perspective view of a holder for use with the apparatus of FIG. 1.

Referring to FIGS. 1 and 2, the holder 30 is a U-shaped member having a front leg 31 and a rear leg 32. The holder is currently intended to be about 2.5 inches wide, 0.75 inches from top to bottom and 1.5 inches from front to back. A slot 33 in the holder is defined by the front leg and the rear leg. As currently preferred, the slot has a wide portion 34 and a narrow portion 35. As discussed further below, the light 40 can be inserted in the wide portion and maintained there by friction. When the light is moved to the narrow portion, the sides of the light are squeezed together, actuating the light. A sleeve may be disposed about the light, increasing its thickness to assure actuation. Of course, other types of openings may be employed to maintain the light in position on the holder in an actuated condition. Further, clasps or straps may also be employed to maintain the light in position on the holder in an actuated condition.

The light 40 is positioned in the slot 33. Acceptable lights are the PAL 110 and the PAL 330 manufactured by Pressalite. These lights are "squeeze" actuated, that is, squeezing the sides of the light actuates the light beam. The slot is sized such that, in the wide portion, the light is held in place by friction but not actuated. In the narrow portion, the light is actuated. If another type of light is employed, the slot should be sized and shaped to hold the light in position in an actuated condition, as the geometry and actuating mechanism of the particular light dictates. Alternatively, the end of a fiber optic cable attached to a light source could be employed as the light and practice the invention.

As currently preferred, the light provides a white light. Other color lights can also be employed. For example, a red light may be preferred in a given application as it provides less disturbance to eyes adjusted to low levels of light. A cover maybe provided to alter the color of the light.

Figure 6:
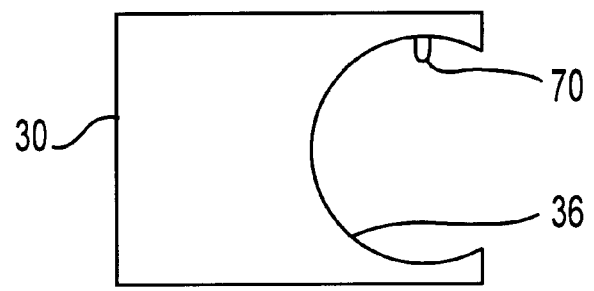
FIG. 6 is a side view of a portion of the holder.

Referring to FIGS. 4A and 6, a channel 36 extends along the front leg 31 of the holder 30. A pin 37 having a cavity 38 is rotatably positioned in the channel. A detent 70 extends into the channel, maintaining the pin in position. Typically, the pin is shorter than the holder and, thus, is contained completely within the front leg. Alternatively, the cavity may be positioned directly in the front leg as shown in FIG. 2.

An edge of a magnifying lens is positioned into the cavity. The lens may be held in the cavity by frictin or an adjesive. Alternatively, the pin could be integrally formed with the lens. Currently, a 3-3/7 inch by 4-7/8 inch rectangular, Fresnel-type lens having a magnification factor of two is preferred. Other types of lenses could also be employed.

The lens defines a field of vision: that area which an operator can see while looking through the lens. The holder 30 is designed to maintain the lens 50 and the light 40 in position such that the light will direct its light beam into the field of vision. In particular, the lens is located in a plane which intersects the axis 42 of the light beam at an angle between 0° and 90°, preferably between 30° and 60°, and most preferably at an angle of about 45°. The angle can be adjusted by rotating the pin in the cavity as the particular application requires.

The portion of the arm 21 connected to the holder 30 extends perpendicular to the rear surface of the holder and, thus, perpendicular to the surface of the slot 33. When the light is inserted in the slot, the portion of the arm connected to the holder is perpendicular to the light and light beam.

The base assembly 20 and the holder 30 are intended for repeated use in a sterile field. Consequently, they must be made of a material capable of being sterilized. The light and magnifying lens are intended for a single use. They are packaged in a sterile condition, typically in the plant of the manufacturer, rather than in a hospital.

To operate the apparatus of the instant invention, the base assembly 20 and the holder 30 are sterilized. One acceptable method of sterilization includes placing the base assembly and the holder in an autoclave. The base assembly and the holder may be sterilized by chemical sterilization, steam or ethylene oxide. Once sterile, the base assembly and the holder are brought into the sterile field and positioned on a support surface. In certain circumstances when the base 22 includes a clamp, the clamp is attached to a support surface 100, such as a Mayo table, in the sterile field.

The light and the lens are preferably contained in a single sterile, sealed package. A sterile pouch contains the package. Alternatively, the lens and the light may be separately packaged. The sterile pouch is opened by a nurse or assistant who need not be sterile. Then, the sterile package is opened by a nurse or assistant who need not be, but can be, sterile. The light 40 is removed from the package by someone who is sterile and is brought into the sterile field. The light is then inserted into the slot 33. When the light is inserted into the narrow portion 35 of the slot, pressure exerted on the sides of the light cause it to actuate. A light beam extends from the light along an axis 42.

Figure 5:
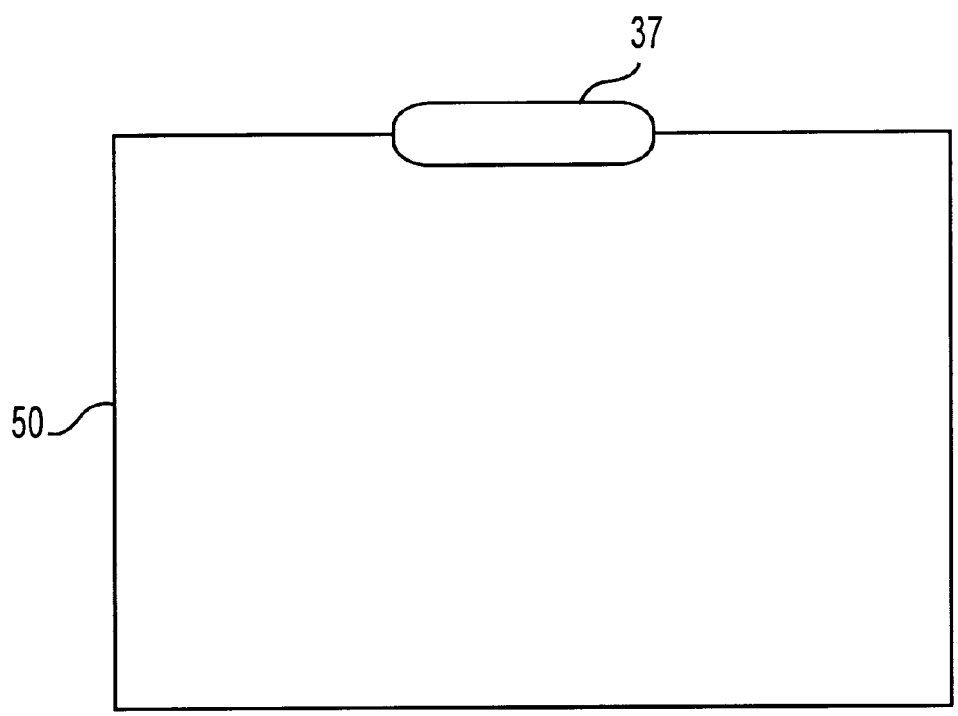
FIG. 5 is a top view of a magnifying lens for use with the apparatus for illuminating and magnifying an object in a sterile field.

The magnifying lens 50, which is attached to the pin 37 (see FIG. 5), is then removed from the package by someone who is sterile and is brought into the sterile field. The pin is inserted into the cavity 38. The tip of the pin may be curved or beveled to better slide under the detent 70. The lens defines a field of vision including the area which can be viewed by a user through the lens. This field of vision changes based, in part, on the lens selected. The light 40 is positioned on the holder 30 with respect to the lens such that the light directs a light beam into the field of vision.

Once the lens 50 and the light 40 are in place on the holder 30, an object to be viewed is positioned in the field of vision and in the path of the light beam. The user can then view the object which is both illuminated and magnified. The magnifying card can be rotated changing the angle between the card and the beam to better view a given object.

While this invention has been described with reference to specific embodiments disclosed herein, it is not confined to the details set forth and the patent is intended to include modifications and changes which may come within and extend from the following claims.

We claim:

1. An apparatus for illuminating and an object in a sterile field for observation comprising:

a base assembly;

a single arm mounted to the base assembly;

a holder mounted to the single arm distal to the base assembly;

a magnifying lens mounted to the holder and defining a field of vision containing the object; and a light attached to the holder in a predetermined spatial relationship with the lens, the light directing a beam of light directly into the field of vision without passing through the magnifying lens;

wherein the object is viewed through the magnifying lens;

wherein the holder comprises a U-shaped member having a front arm and a rear arm, the rear arm is attached to the base assembly and the light is positioned between the front arm and the rear arm;

wherein the light has an axis and the magnifying lens is in a plane which intersects the axis of the light at an angle of about 45°.

2. The apparatus of claim 1 further comprising a pin rotatably seated in a channel disposed in the holder, wherein a cavity is disposed on the pin and the magnifying lens is seated in the cavity.

3. The apparatus of claim 1 wherein the front arm and the rear arm define an opening which is shaped to actuate the light when the light is in the opening.

4. The apparatus of claim 1 wherein the base assembly includes a clamp, the clamp comprising a lower member fixed to the arm and a locking member selectively positioned on the arm by a ratchet.

5. The apparatus of claim 1 wherein the arm further includes a swivel joint.

6. The apparatus of claim 1 wherein the arm further includes a bending joint.

7. The apparatus of claim 1 wherein the arm is flexible.

8. The apparatus of claim 1 wherein the holder is sterile, the magnifying lens is sterile and the light is sterile.

9. A method of illuminating and magnifying an object in a sterile field without contaminating the sterile field using an apparatus having a base assembly, a holder mounted at one end of the base assembly, a magnifying lens mounted to the holder, and a light mounted to the holder in a predetermined spatial relationship with the magnifying lens, the method comprising:

positioning the base assembly in a sterile field, including clamping the base to a fixed surface;

opening a sterile pack containing the light in a sterilized condition and moving the light into the sterile field;

mounting the light to the holder;

actuating the light and providing a light beam;

removing the magnifying lens from the sterile pack and moving the lens into the sterile field;

attaching the lens to the holder in a predetermined spatial relationship with the light which lens defines a field of vision such that the light beam intersects the field of vision; and bringing an object into the field of vision.

10. The method of claim 9 further comprising sterilizing the base assembly and the holder.

11. The method of claim 10 wherein sterilizing the base assembly comprises sterilizing the base assembly in an autoclave.

12. The method of claim 9 wherein the light is actuated as it is inserted into an opening in the holder.

13. The method of claim 9 wherein attaching the magnifying lens to the holder comprises inserting an edge of the magnifying lens into a channel in the holder.

14. The method of claim 9 wherein the light is contained in a light pack and the magnifying lens is contained in a lens pack.

15. An apparatus for illuminating and magnifying a field of vision in a sterile field comprising:

an autoclavable base assembly;

an autoclavable holder mounted at one end of the base assembly and having a slot extending through the holder;

a sterile light selectively positioned in the slot in a first position or a second position wherein, in the first position, the light is off and, in the second position, the light is actuated, directing a beam of light into the field of vision;

a sterile magnifying lens attached to the holder in a predetermined spatial relationship with the light;

a pin fixedly mounted to an edge of the magnifying lens and rotatable seated in a channel in the holder.

16. The apparatus of claim 15 wherein the base assembly comprises a positionable arm.

\* \* \* \* \*